US009622821B2

(12) United States Patent
Gopalakrishna et al.

(10) Patent No.: US 9,622,821 B2
(45) Date of Patent: Apr. 18, 2017

(54) SYSTEM AND METHOD FOR STRUCTURE-FUNCTION FUSION FOR SURGICAL INTERVENTIONS

(71) Applicant: Carnegie Mellon University, Pittsburgh, PA (US)

(72) Inventors: Prahlad Menon Gopalakrishna, Pittsburgh, PA (US); Daniel Ryder Ludwig, Maple Glen, PA (US); David Schwartzman, Pittsburgh, PA (US)

(73) Assignees: University of Pittsburgh—Of the Commonwealth System of Higher Education, Pittsburgh, PA (US); Carnegie Mellon University, Pittsburgh, PA (US)

( * ) Notice: Subject to any disclaimer, the term of this patent is extended or adjusted under 35 U.S.C. 154(b) by 186 days.

(21) Appl. No.: 14/434,434

(22) PCT Filed: Oct. 11, 2013

(86) PCT No.: PCT/US2013/064484
§ 371 (c)(1),
(2) Date: Apr. 9, 2015

(87) PCT Pub. No.: WO2014/059241
PCT Pub. Date: Apr. 17, 2014

(65) Prior Publication Data
US 2015/0257845 A1 Sep. 17, 2015

Related U.S. Application Data

(60) Provisional application No. 61/795,152, filed on Oct. 11, 2012.

(51) Int. Cl.
*A61B 6/00* (2006.01)
*A61B 19/00* (2006.01)
(Continued)

(52) U.S. Cl.
CPC .............. *A61B 19/50* (2013.01); *A61B 6/503* (2013.01); *A61B 6/5229* (2013.01); *A61B 34/10* (2016.02); *A61B 34/20* (2016.02); *G06T 3/00* (2013.01); *A61B 5/0422* (2013.01); *A61B 5/062* (2013.01); *A61B 6/507* (2013.01); *A61B 90/39* (2016.02); *A61B 2034/107* (2016.02);
(Continued)

(58) Field of Classification Search
CPC ......... A61B 6/503; A61B 34/20; A61B 19/50; A61B 34/10; A61B 6/5229; A61B 2090/363; A61B 6/507; A61B 5/0422; A61B 5/062; A61B 2576/023; A61B 2034/107; A61B 2090/374; A61B 2090/3762; G06T 3/00; G06T 2207/30048; G06T 2207/10108; G01R 33/4808
See application file for complete search history.

(56) References Cited

U.S. PATENT DOCUMENTS

| | | | |
|---|---|---|---|
| 2005/0148859 A1* | 7/2005 | Miga | G06K 9/6211 600/410 |
| 2008/0071143 A1* | 3/2008 | Gattani | A61B 1/00009 600/117 |
| 2010/0240996 A1* | 9/2010 | Ionasec | G06T 7/0016 600/443 |

* cited by examiner

*Primary Examiner* — Bo J Peng
(74) *Attorney, Agent, or Firm* — Tucker Arensberg, P.C.

(57) ABSTRACT

A method for fusing information related to structural features and characteristics of a biological sample. The resulting fused image may be imported into a surgical navigation technology intra-operatively to aid in surgical interventions by co-registering the fused image with the patient's anatomical features.

48 Claims, 16 Drawing Sheets

(51) Int. Cl.
  G06T 3/00     (2006.01)
  A61B 34/20    (2016.01)
  A61B 34/10    (2016.01)
  *A61B 5/042*      (2006.01)
  *A61B 5/06*       (2006.01)
  *G01R 33/48*      (2006.01)
  *A61B 90/00*      (2016.01)

(52) U.S. Cl.
  CPC ............... *A61B 2034/2051* (2016.02); *A61B 2034/2065* (2016.02); *A61B 2090/363* (2016.02); *A61B 2090/365* (2016.02); *A61B 2090/374* (2016.02); *A61B 2090/3762* (2016.02); *A61B 2576/023* (2013.01); *G01R 33/4808* (2013.01); *G06T 2207/10108* (2013.01); *G06T 2207/30048* (2013.01)

SYSTEM AND METHOD FOR STRUCTURE-FUNCTION FUSION FOR SURGICAL INTERVENTIONS

CROSS-REFERENCE TO RELATED APPLICATIONS

This application claims priority under 35 U.S.C. §119(e) to U.S. Provisional Patent Application No. 61/795,152, filed on Oct. 11, 2012, entitled "Structure-Function Fusion for Cardiac Interventions." This application is hereby incorporated by reference in its entirety.

BACKGROUND

Many surgical interventions require the accurate insertion and orientation of one or more surgical instruments. For example, in interventional cardiology, this may relate primarily to a insertion and orientation of a catheter or electrical lead, into a tissue region of heart or in the vascular network, in a predetermined trajectory. Pre-operative planning for such procedures conventionally depends upon two-dimensional radiographic images typically in two orthogonal view directions, making it difficult to determine the shape and structure of regions of interest during surgery. Although rudimentary image processing for volumic image reconstruction, region of interest masking and image enhancement techniques can significantly aid interpretation of two dimensional image planes, a significant lapse exists between interpreting functional radiological images seen at the pre-surgical stage and the actual patient anatomical structures at the operating table. Correlation of exact anatomical locations of interest from structurally less accurate (and often skewed) functional image data, such as SPECT, is challenging. Preliminary primary and secondary research as well as information in the literature has indicated that it is not uncommon for biomedical imaging research groups and medical centers to utilize in-house codes as well as advanced commercial face recognition technology (such as those developed by Fuji, Sony, Microsoft, etc.) to fuse structurally accurate computed tomography (CT) or magnetic resonance imaging (MRI) data with information obtained from positron emission tomography (PET), ultrasound and fluoroscopy data. Such co-registration has admittedly increased diagnostic accuracy and specificity during interventional treatments across surgical specialties, including orthopedics, cardiovascular and neurosurgery. However, the ability to introduce these data into the operating room has still been found wanting.

Cardiac resynchronization therapy (CRT), at present, confers no benefit to at least 30% of patients referred for therapy, a significant limitation of this invasive and expensive treatment. Left ventricular lead placement is an important determinant in response to therapy, with CRT conferring optimal benefit when the left ventricle lead is localized to the latest-activating, non-scarred region. At present, left ventricle lead implantation is essentially empiric; that is, performed with limited consideration of the patients' left ventricle scar or mechanical activation features. This is despite the fact that such information is readily available using non-invasive imaging techniques. There exists a need for a method for intra-operatively guiding left ventricle lead implantation.

Another example of a procedure that remains challenging is catheter ablation of ischemic ventricular tachycardia (VT). Common hindrances include the long duration often required to adequately characterize the substrate, as well as pleomorphism and/or hemodynamic intolerance of induced tachycardias. Long duration and lack of predictability conspire to decrease operator enthusiasm for the procedure, relegating it to use primarily in patients who experience inefficacy or toxicities of antiarrhythmic drugs. Antiarrhythmic drug use in typical ablation candidates may not be for the best. VT ablation would benefit by more routinely including an empiric, "anatomic" element, akin to pulmonary vein isolation.

There are a number of state of the art technologies for 3-dimensional electroanatomic mapping systems that are currently used in the clinic. Such systems can primarily be classified into those that: a) are dependent upon impedance measurements between individual catheter electrodes and patches placed on a patient's chest and abdomen; and b) utilize magnetic location technology to provide accurate visualization of the magnetosensor-equipped catheter tips. Extensive studies have also been conducted to compare different available techniques for specific surgeries and the latter magnetic-based three dimensional mapping system has been proven to be superior for time-critical interventions involving fluoroscopy and radiofrequency energy delivery time in comparison with current-based system.

There exists a need for improved imaging and data fusion techniques and a method for introducing this fused data into the operating room. The present invention enables image fusion from multiple medical imaging modalities and allows introduction of the resulting fused data into the operating room, registered against the patient anatomy, in tandem with current surgical navigation technology.

SUMMARY

The present disclosure relates generally to image-guided surgical interventions. More specifically, the present disclosure provides for a method for fusing multiple imaging data sets to generate a fused color image correlating various characteristics of a biological sample with structural features.

In one embodiment, the present disclosure provides for a method for fusing structural information with information associated with at least one characteristic of a biological sample using both rigid and non-rigid transformations and nearest neighbor algorithms. At least one medical imaging data set may be acquired representative of at least a portion of a biological sample. A first set of volume image data may be segmented from the medical imaging data set to generate a surface comprising a plurality of points. A second set of volume image data associated with at least one characteristic of the biological sample may be selected from the medical imaging data. A plurality of spatial fiducials may be used to rigidly and non-rigidly transform the second set of imaging data onto the surface. The second set of imaging data may then be re-sampled onto the surface to generate a fused image wherein each color is indicative of at least one characteristic at that location in the sample.

In another embodiment, the present disclosure also provides for a method of fusing structural information with information associated with at least of a biological sample using a standard form. At least one medical imaging data set representative of a biological sample may be acquired. A first set of volume image data associated with at least one structure may be segmented from the medical imaging data set to generate a surface comprising a plurality of points. A second set of volume image data associated with at least one characteristic of the biological sample may be selected from the medical imaging data set. A plurality of spatial fiducial markers may be selected on the surface and the second set of volume image data. The second set of volume image data may be transformed into a standard form wherein each point on the standard form maintains characteristic data. Rigid transformation techniques may be applied to spatially transform the standard form into a virtual spatial location comprising the structure. Non-rigid transformation techniques may be applied to warp at least a portion of the standard form onto the surface. A plurality of points on the surface may be correlated with a plurality of points of the standard form by applying at least one nearest neighbor algorithm. The second set of volume image data may then be re-sampled onto the surface to generate a fused color image wherein each color is indicative of at least one characteristic at that location in the biological sample.

In another embodiment, the present disclosure also provides for a method of fusing structural information with information associated with at least one characteristic of a biological sample by converting a standard form into at least one volume image. At least one medical imaging data set may be acquired. A first set of volume image data associated with a structure of the sample may be segmented from the medical imaging data set to generate a surface. A second set of volume image data associated with at least one characteristic of the sample may be selected from the medical imaging data set. A plurality of spatial fiducial markers may be selected on the surface and the second set of volume image data. The second set of volume image data may be transformed into a standard form wherein each point on the standard form maintains characteristic data. The standard form may be transformed into a third set of volume image data. The surface may be transformed onto the third set of volume image data using the plurality of spatial fiducials. Each of a plurality of points of the surface may be correlated with at least one characteristic of the biological sample by applying at least one nearest neighbor algorithm. The third set of volume image data may be re-sampled onto the surface at each of a plurality of points based on this correlation to generate a fused color image wherein each color is indicative of at least one characteristic at that location in the biological sample.

The method provided herein overcomes the limitations of the prior art by providing a clinician with more robust patient data that can be used pre-operatively and intra-operatively to aid the planning and execution of surgical interventions. The present disclosure contemplates that the method may be applied to assess specific structures and characteristics of interest, depending on a patient's medial history and treatment plan, to generate a custom-processed model that is specific to the patient. For example, characteristics such as morphology, perfusion, mechanical function, and electrophysiology may be combined using one or more algorithmic techniques and rendered onto an anatomically accurate model of one or more structures of a patient, such as the heart. A clinician may use this information-rich image to decide what surgical interventions a patient should undergo and improve the results of those interventions. For example, this fused color image may be supplied directly into a surgical navigation system in the operating room by way of device-compatible software plug-ins.

BRIEF DESCRIPTION OF THE DRAWINGS

The accompanying drawings, which are included to provide further understanding of the disclosure and are incorporated in and constitute a part of this specification illustrate embodiments of the disclosure, and together with the description, serve to explain the principles of the disclosure.

In the drawings:

FIG. 6 illustrates the intermediary step of transforming volume image data associated with sample characteristics into a standard form such as a polar plot. The polar plot is warped onto a surface to generate a fused image representative of both the structure and the underlying characteristics of the biological sample.

FIG. 8 illustrates the intermediary step of transforming a standard form into a set of volume image data. The surface is transformed onto the volume image data to generate a fused image representative of both the structure and the underlying characteristics of the biological sample.

FIG. 12 illustrates the use of SPECT and CT data.

FIG. 14 illustrates the identification of the phrenic nerve.

FIG. 15 illustrates left ventricle lead guidance and location confirmation.

FIG. 16A illustrates the correspondence of a site of latest activation from SPECT data and electrical mapping and FIG. 16B illustrates the correspondence of scar information from SPECT data with voltage.

DETAILED DESCRIPTION

Reference will now be made in detail to the embodiments of the present disclosure, examples of which are illustrated in the accompanying drawings. Wherever possible, the same reference numbers will be used throughout the specification to refer to the same or like parts.

The present disclosure provides for a method of fusing multiple types of data corresponding to information relating to the structure and underlying characteristics of a biological sample. The present disclosure contemplates that this method may be applied to the analysis of any biological sample. The sample may comprise, but is not limited to, at least one of: a cell, a tissue, an organ, a organ system, a vein, an artery, a nerve, a tendon, and a muscle. The present disclosure contemplates that a structure may comprise at least a portion of a biological sample. For example, the structure may comprise a whole organ, such as the heart, or a specific region of interest associated with a portion of the whole organ, such as the left ventricle A variety of characteristics may be selected for analysis using the method provided herein and the method may analyze one or a plurality of different characteristics of a patient. Examples of characteristics may include perfusion, morphology, mechanical function, and electrophysiology. However, the present disclosure is not limited to these characteristics and it is contemplated that any characteristic known in the art may be analyzed.

Figure 1:
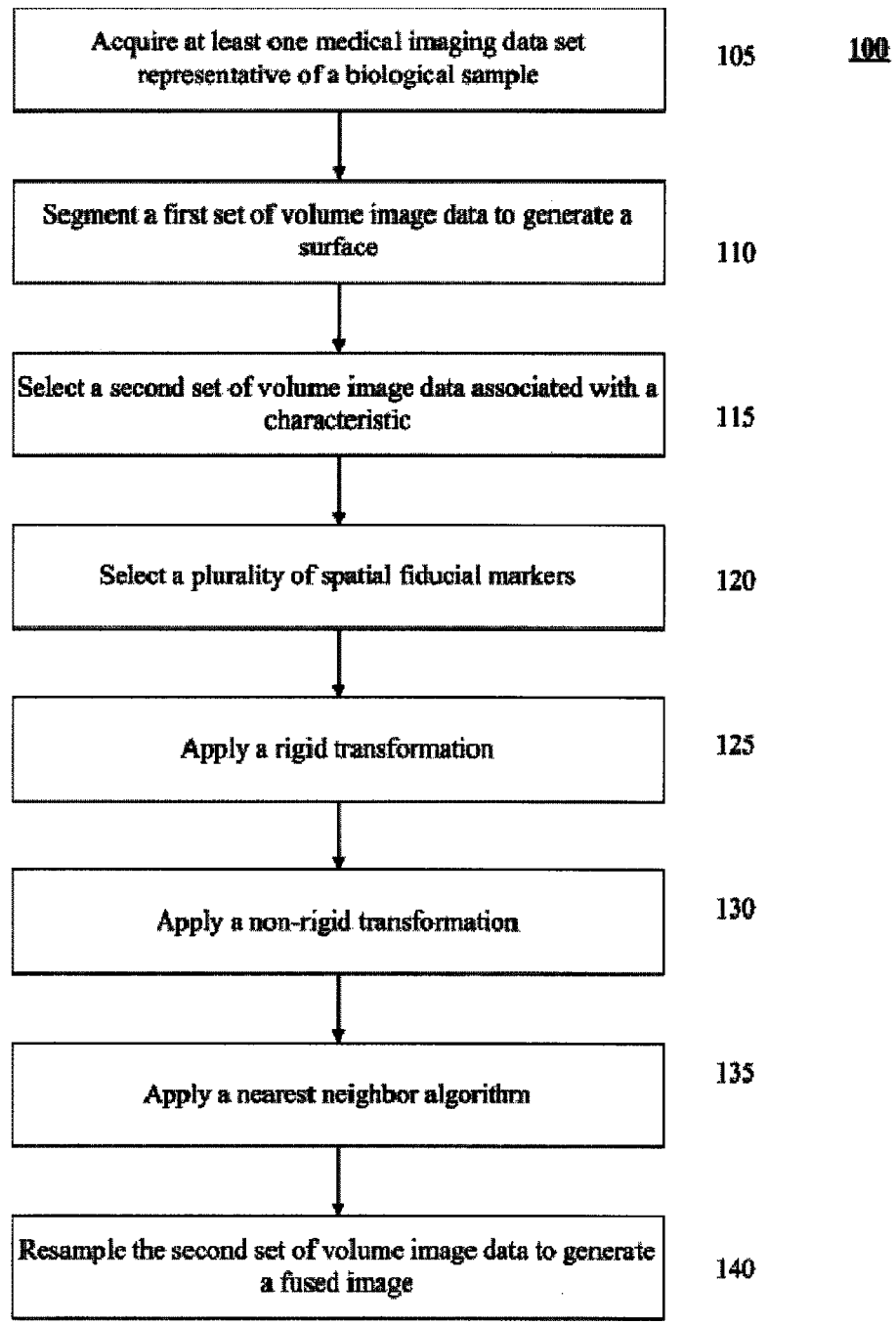
FIG. 1 is illustrative of a method of the present disclosure.

In one embodiment, illustrated by FIG. 1, the method 100 may comprise acquiring at least one medical imaging data set representative of at least one biological sample in step 105. The embodiments presented in this disclosure contemplate that more than one medical imaging data set may be acquired. In such an embodiment, the data sets may be generated using the same modality or two or more different modalities. Any modality known in the art may be used including, but not limited to: SPECT, CT, MRI, PET, x-ray, and fluoroscopy.

The biological sample may comprise at least one structure and each medical imaging data set may comprise volume image data. The volume image data may comprise a plurality of voxels which are representative of data in at least three dimensions. Each volume image may comprise a plurality of two-dimensional image planes comprising a plurality of pixels.

In step 110 a first set of volume data may be segmented from the medical imaging data set to generate a surface comprising a plurality of points. This first set of volume data may comprise a plurality of voxels associated with at least one structure of the biological sample.

A second set of volume image data may be selected in step 115. This second set of volume image data may comprise a plurality of voxels associated with at least one characteristic of the biological sample. The characteristic may be a magnitude of at least one physically relevant parameter of the sample and the magnitude may be expressed as at least one color. Throughout this disclosure and the various embodiments, it is contemplated that intensity is a physically relevant parameter.

The embodiments presented herein contemplate that the magnitude may further comprise a range of values wherein the color may further comprise an arbitrary color gradient correlated with the range of values. In one embodiment, this color may comprise at least one of: full color and gray scale. In another embodiment, a plurality of characteristics (and their associated magnitudes) may be combined using algorithmic techniques to display a result that depicts more than one characteristic. In this embodiment, each characteristic may be associated with a different color or they may be associated with the same color. This technique may be referred to herein as coalescence, or that the characters are coalesced.

In step 120, a plurality of spatial fiducial markers may be selected on the surface and on the second set of volume image data. Throughout the disclosure and in reference to the various embodiments, spatial fiducial markers may comprise at least one of surface fiducials or fiducials inside the body These spatial fiducial markers may be used to spatially transform the second set of volume image data into a virtual spatial location comprising the segmented structure. In one embodiment, illustrated by step 125, this spatial transformation may be achieved by applying at least one rigid transformation. In step 130, at least one non-rigid transformation may be applied to warp at least a portion of the second set of volume image data onto the surface.

To correlate each of a plurality of points of the surface with at least one voxel associated with the second set of volume image data, at least one nearest neighbor algorithm may be applied in step 135. In step 140, the second set of volume data may be re-sampled onto the surface at each of a plurality of points based on this correlation. The result may be a fused image, wherein the fused image comprises a color image representative of the surface of the biological sample, wherein each color is indicative of at least one characteristic at that location in the biological sample.

Figure 2:
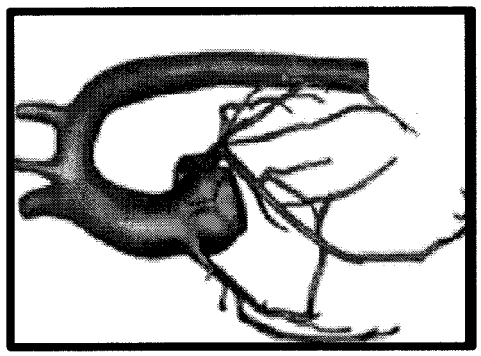
FIG. 2 is representative of the structure-structure fusion capabilities of the present disclosure.
Figure 2:
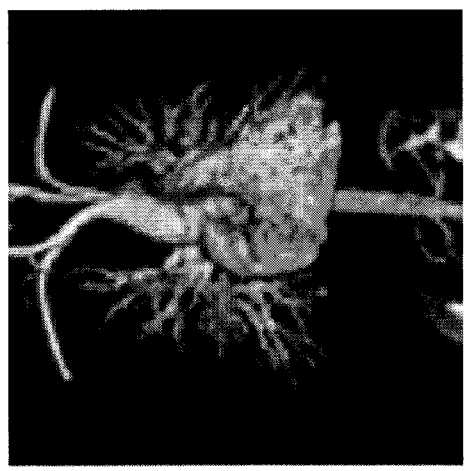
Figure 2:
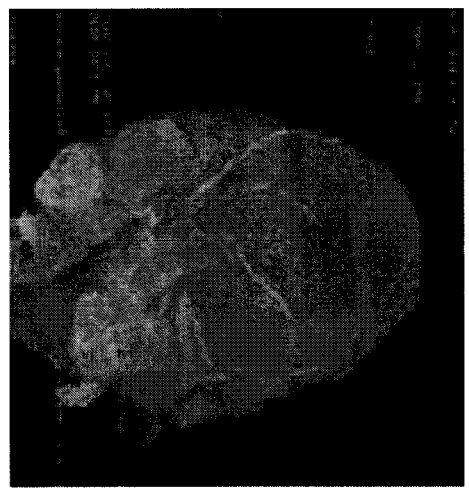

In one embodiment of the present disclosure, two or more medical imaging data sets may be generated using two or more different medical imaging modalities to ascertain robust structural information. Sets of volume image data from different modalities may be combined to generate an image that provides more structural features that either set of volume image data alone. As illustrated in FIG. 2, volume image data from a first modality 205 may be fused with volume image data from a second modality 210 to generate fused structural information 215. In FIG. 2, a CT scan of the heart 205 may capture coronary arteries but may be truncated at the base. MRI 210 may capture the aorta but the coronary arteries cannot be clearly identified. The structure-structure fusion image 215 represents the two data sets stitched together at the aortic root into a single model after appropriate shape-based rigid registration. This fusion may be accomplished using known techniques. The resulting fused structural data may then be used in conjunction with one or more of the embodiments provided herein to further fuse characteristic information onto a surface, wherein the surface is now representative of the fused structural features.

Figure 3:
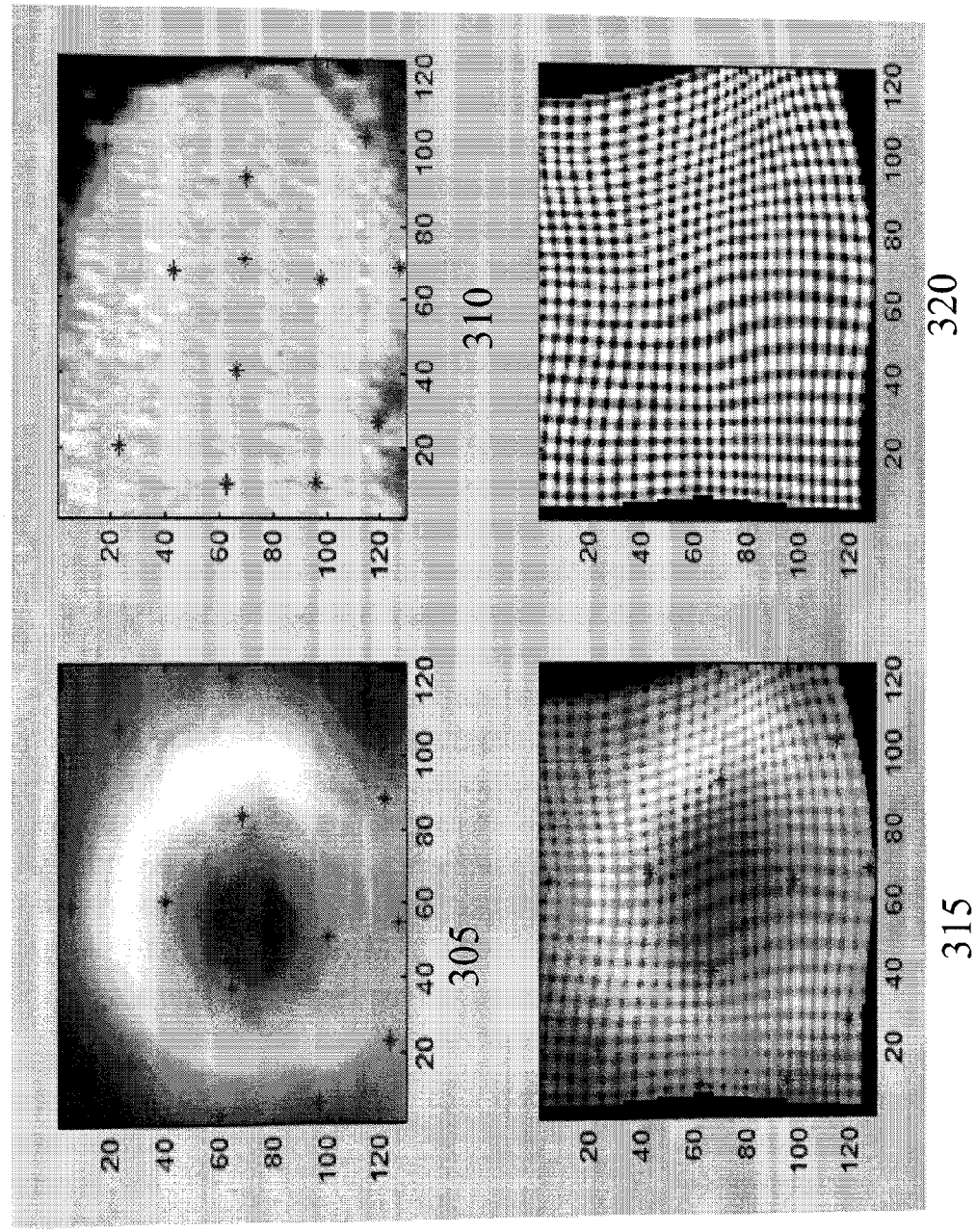
FIG. 3 is representative of affine registration by warping of data. A plurality of spatial fiducial markers is illustrated.
Figure 4:
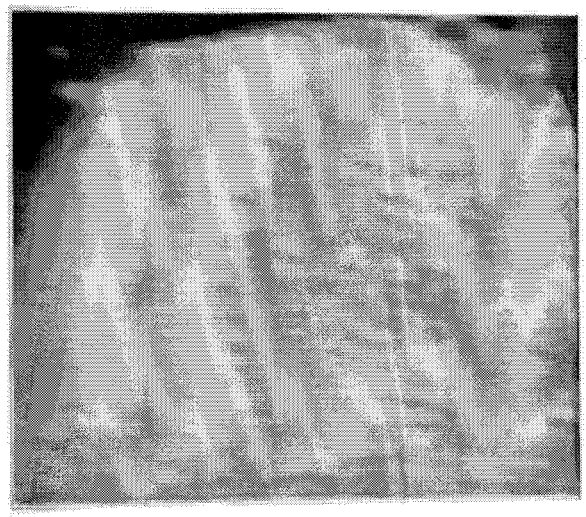
FIG. 4 is representative of the data fusion capabilities of the present disclosure. SPECT data is warped onto CT data to generate a fused image representative of both the structure and the underlying characteristics of the biological sample.
Figure 4:
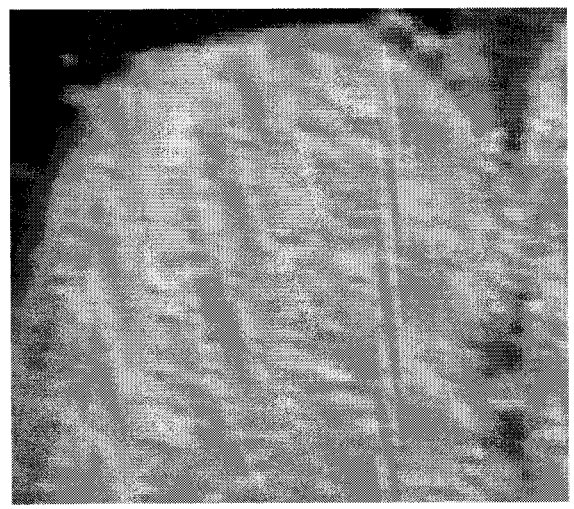
Figure 4:

FIG. 3 is illustrative of the fusion capabilities of the present disclosure. Specifically, FIG. 3 is representative of the resulting fusion that may be achieved by applying the method steps of FIG. 1. Referring to FIG. 3, 305 illustrates a plurality of spatial fiducial markers selected on SPECT data. A plurality of spatial fiducal markers selected on CT data is illustrated in 310. Rigid and non-rigid transformations are shown in 315 and 320. The resulting fusion image is illustrated in FIG. 4. Here, the SPECT data 405 is fused with the CT data 410 to generate a fused image 415. The fused image 415 comprises a color image representative of the surface of the biological sample wherein each color is indicative of at least one characteristic at that location in the sample.

Figure 5:
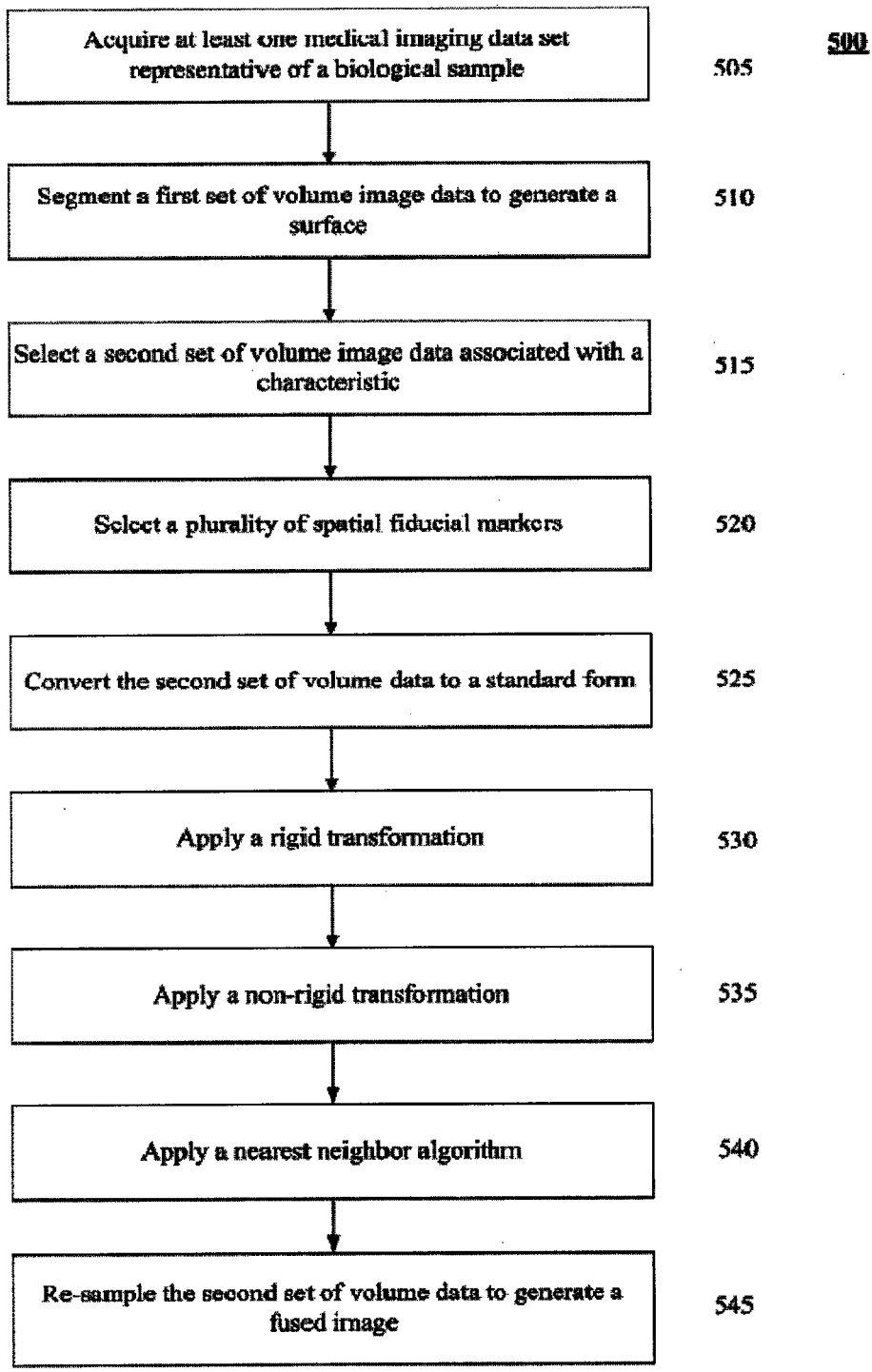
FIG. 5 is illustrative of a method of the present disclosure.

In another embodiment, illustrated by FIG. 5, the method 500 may comprise acquiring at least one medical imaging data set representative of at least one biological sample in step 505. As in the previous embodiment, the biological sample may comprise at least one structure and each medical imaging data set may comprise volume image data comprising a plurality of voxels representative of data in at least three dimensions. Each volume image may comprise a plurality of two-dimensional image planes comprising a plurality of pixels. In step 510, a first set of volume image data comprising a plurality of voxels associated with at least one structure of the biological sample may be segmented from the medical imaging data set to generate a surface comprising a plurality of points.

In step 515, a second set of volume image data may be selected. The second set of volume image data may comprise a plurality of voxels associated with at least one characteristic of the biological sample. The characteristic may be a magnitude of at least one physically relevant parameter of the biological sample, wherein the magnitude is expressed as at least one color.

A plurality of spatial fiducial markers may be selected on the surface and the second set of volume image data in step 520. In step 525 the second set of volume image data may be converted into a standard form, wherein each point on the standard form maintains characteristic data. In one embodiment, this standard form may comprise at least one polar plot (also referred to as a "bulls-eye plot"). Other standard forms known in the art may also be used.

At least one rigid transformation may be applied in step 530 to spatially transform the standard form into a virtual spatial location comprising the structure using the plurality of spatial fiducial markers. In step 535 the plurality of spatial fiducial markers may be used to warp at least a portion of the standard form onto the surface. In one embodiment, this warping may be achieved by applying at least one non-rigid transformation.

To correlate each of a plurality of points on the surface with at least one point on the standard form, at least one nearest neighbor algorithm may be applied in step 540. In step 545, the second set of volume image data may be re-sampled onto the surface at each of a plurality of points based on this correlation to generate a fused image. In one embodiment, the fused image may comprise a color image representative of the surface, wherein each color is indicative of at least one characteristic at that location in the biological sample.

Figure 6:
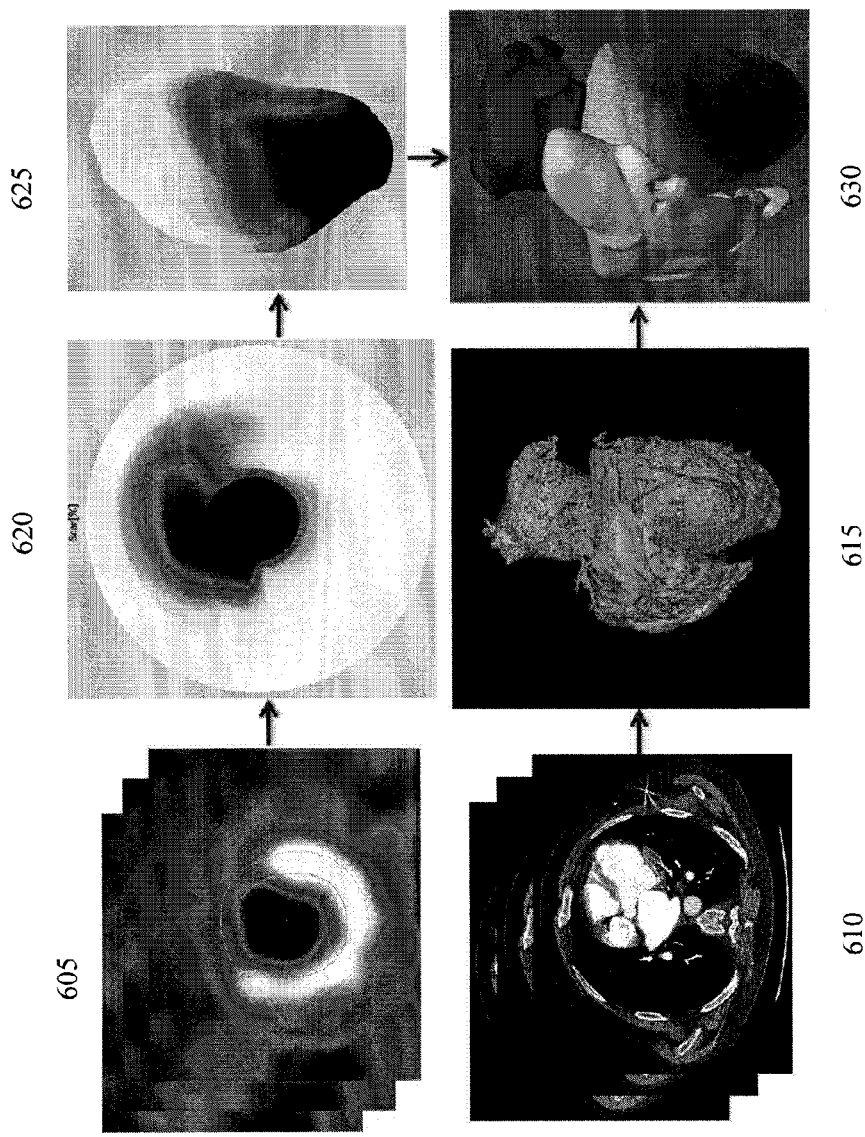
FIG. 6 is representative of the data fusion capabilities of the present disclosure. SPECT data is warped onto CT to generate a fused image representative of both the structure and the underlying characteristics of the biological sample.

FIG. 6 is illustrative of the fusion capabilities of the present disclosure. Specifically, FIG. 6 illustrates the fusion capabilities of the embodiment illustrated in FIG. 5 comprising the conversion of a second set of volume image data into a standard form. SPECT data 605 and CT data 610 were acquired. A first set of volume image data is extracted to generate a surface 615 comprising a plurality of points. A second set of volume image data associated with at least one characteristic of the biological sample is selected and converted into a standard form using a method known in the art 620. The standard form represented in FIG. 6 is a polar plot illustrating scar transmurality as a percentage. The second set of volume data is warped onto the structure 625 and a fused image generated 630 wherein the fused image comprises a color image representative of the surface wherein each color is indicative of at least one characteristic at that location in the biological sample.

Figure 7:
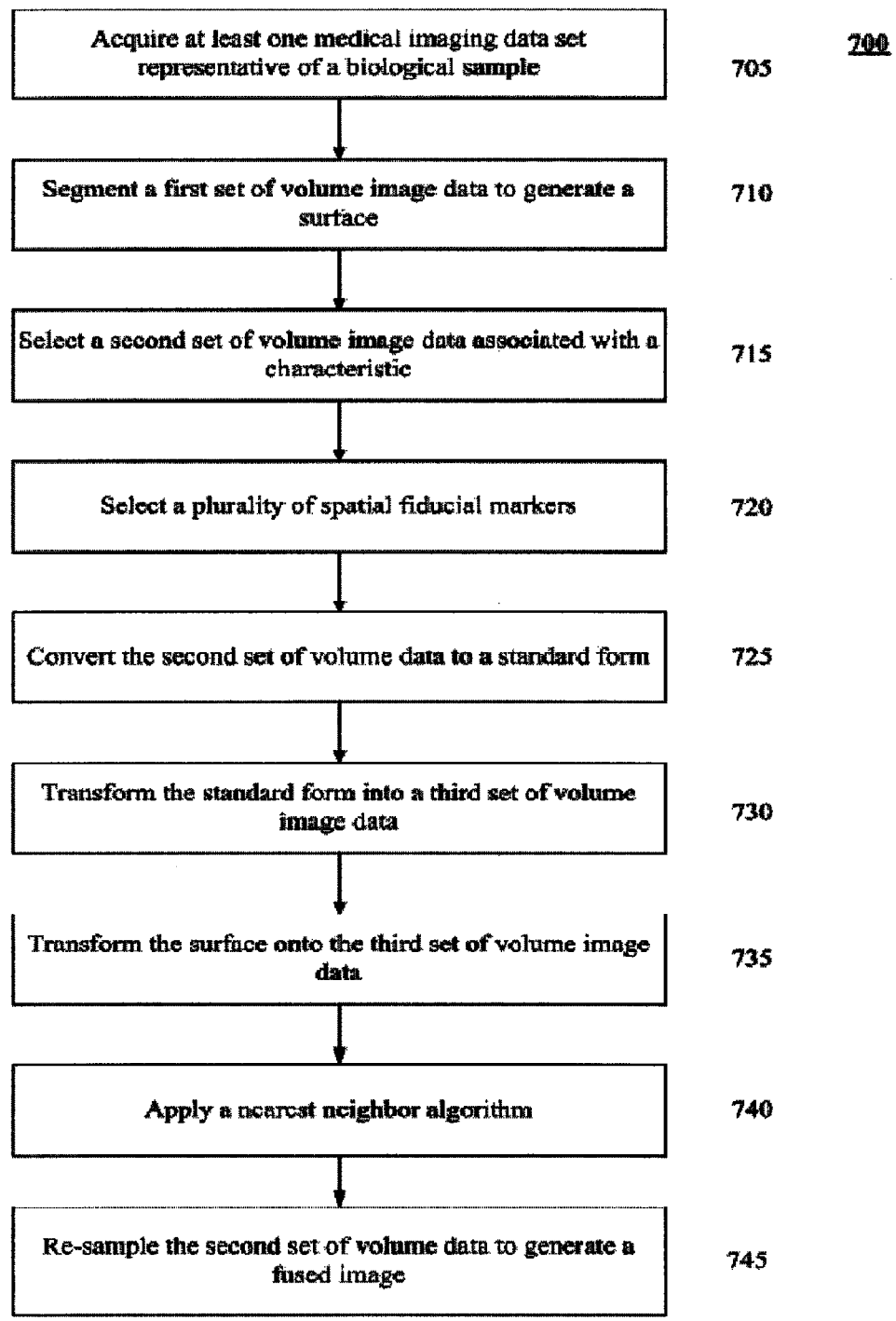
FIG. 7 is illustrative of a method of the present disclosure.

In yet another embodiment, illustrated by FIG. 7, the method 700 may comprise acquiring at least one medical imaging data set representative of at least one biological sample in step 705. As in the previous embodiment, the biological sample may comprise at least one structure and each medical imaging data set may comprise volume image data comprising a plurality of voxels representative of data in at least three dimensions. Each volume image may comprise a plurality of two-dimensional image planes comprising a plurality of pixels. In step 710, a first set of volume image data may be segmented from the medical imaging data set to generate a surface comprising a plurality of points. In one embodiment, the first set of volume image data may comprise a plurality of voxels associated with at least one structure of the biological sample. In step 715, a second set of volume image data comprising a plurality of voxels associated with at least one characteristic of the biological sample may be selected. In one embodiment, the characteristic may be a magnitude of at least one physically relevant parameter of the sample, wherein the magnitude is expressed as at least one color.

A plurality of spatial fiducial markers may be selected on the surface and on the second set of volume image data in step 720. The second set of volume image data may be converted into a standard form in step 725, wherein each point on the standard form maintains the characteristic data. In step 730, the standard form may be transformed into a third set of volume image data comprising a plurality of voxels representative of data in at least three dimensions. Each voxel may be associated with at least one characteristic. In step 735, the surface may be transformed onto the third set of volume image data using the plurality of spatial fiducial markers. Each of a plurality of points of the surface may be correlated with at least one voxel of the third set of volume image data by applying at least one nearest neighbor algorithm in step 740. In step 745, the third set of volume image data may be re-sampled onto the surface at each of a plurality of points based on this correlation to generate a fused image. The fused image may further comprise a color image representative of the surface, wherein each color is indicative of at least one characteristic at that location in the biological sample.

Figure 8:
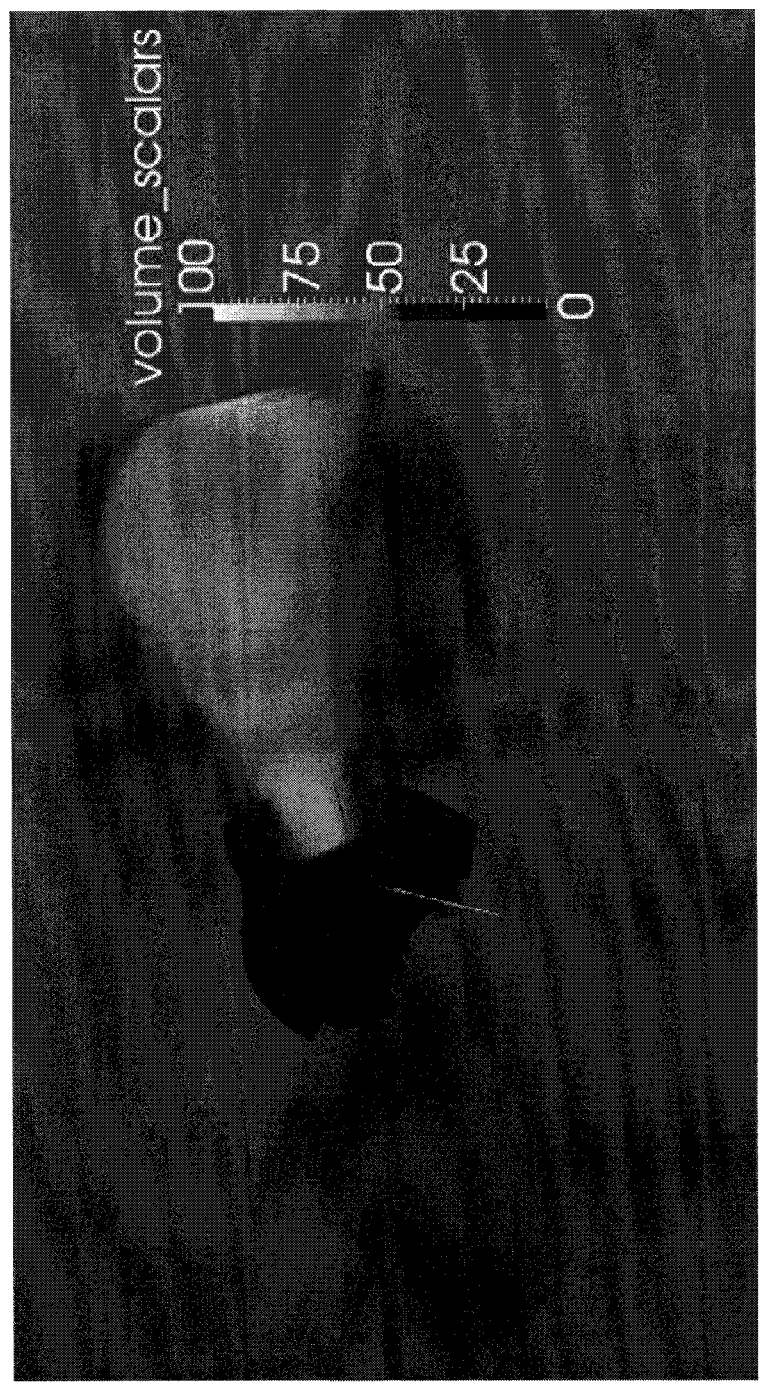
FIG. 8 is representative of the data fusion capabilities of the present disclosure.

Transformation of the standard form into a third set of volume image data is represented in FIG. 8. Application of nearest neighbor algorithm correlates each of a plurality of points on the surface with at least one voxel. Re-sampling can then be applied to generate the fused image.

The result of a method relating to any of these embodiments is a fused image that can be imported into the operating room using a surgical navigation technology with the capability of performing landmark/fiducial based registration between the imported data and the patient's anatomy. In one embodiment, the fused image may be co-registered with the patient's anatomy by associating the fused image with at least one surgical too, where the surgical tool is tracked electromagnetically in the patient's body.

While some of the examples provided herein relate to the field of cardiac surgical interventions, this disclosure is not limited to only cardiac surgery and may be applied in a variety of other non-cardiac interventions as well. Examples of cardiac interventions that may apply the methods herein include, but are not limited to: angioplasty, artificial heart valve surgery, atherectomy, bypass surgery, cardiomyoplasty, heart transplant, minimally invasive heart surgery, radiofrequency ablation, atrial fibrillations, cardiac resynchronization therapy, VT, stent procedures, transmyocardial revascularization. Other non-cardiac procedures that may apply this method may include: catheter ablations, catheter guidance, drug delivery, biopsy, tumor excision/ablation, and biomaterial introduction.

Figure 9:
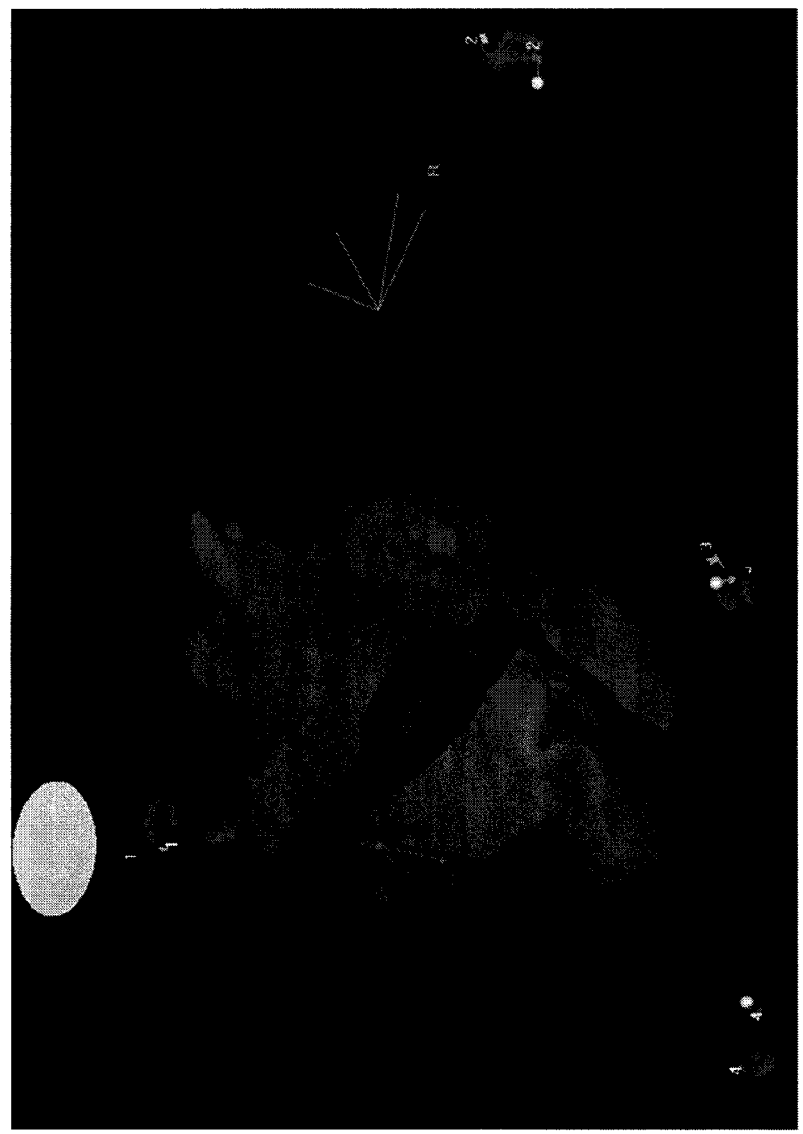
FIG. 9 is representative of the image-guided intervention capabilities of the present disclosure.

For example, FIG. 9 is a representation of the fused image imported into a Carto® surgical navigation platform. The fusion of characteristics relating to scar and mechanical dysynchronay of the left ventricle of the heart (extracted from SPECT and cardiac MRI, respectively) along with anatomical surfaces representing the four chambers of the heart and the coronary venous anatomy (segmented from CT). In this example, the clinician's catheter (illustrated in the Figure) is navigated through the fused image while simultaneously navigating the patient's heart. Such navigation is enabled because the patient's anatomy is co-registered with the used image model by virtue of surface fiducal markers placed at identical locations during the CT scan and during the intervention.

Additional specific examples of surgical interventions that may benefit from the method disclosed herein include, but are not limited to: fluoroscopy guided surgery for pulmonary vein antrum isolation treatment, intracardiac echocardiography and a roaming circular mapping catheter for treatment of arterial fibrillation and other cardiac arrhythmias, cardiac resynchronization therapy, image guided installation of CRT pacemaker by registration of SPECT against cardiac CT anatomic data, electro-anatomic mapping with cardiac MRI to guide catheter manipulation, catheter mapping and ablation, precutaneous coronary interventions, image-guided surgery for implantation of vascular stents, and active non-invasive monitoring of the pre-operative state and post operative recover in patients, including those with heart disease.

Example 1

Figure 10:
FIG. 10 is representative of the data fusion capabilities of the present disclosure, the panels providing pre-ablation images.
Figure 11:
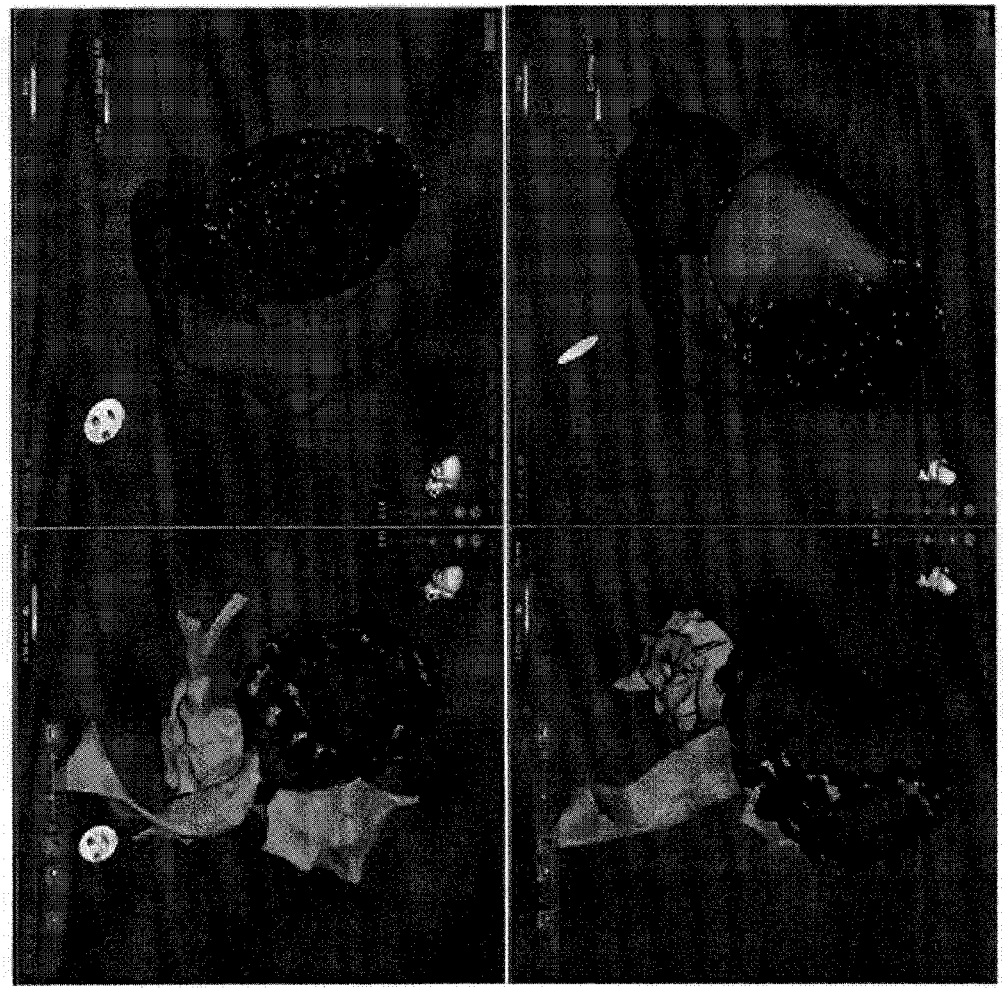
FIG. 11 is representative of the data fusion capabilities of the present disclosure, the panels providing post-ablation images.

FIGS. 10 and 11 are representative of the fusion capabilities of the present disclosure and the potential of applying such fusion techniques to aid in the planning and execution of surgical interventions. The data refers to catheter ablation of VT.

Referring to FIG. 10, 1005 is an endocardial Fast Anatomical Mapping-derived image (anterior oblique) of the left ventricle of the heart and 1006 is an endocardial Fast Anatomical Mapping-derived image (left lateral) of the left ventricle of the heart. A SPECT-Multi-detector computed tomography (MDCT) fusion image after registration corresponding to left ventricle of the heart (anterior oblique) is shown by 1007, and 1008 is a SPECT-MDCT fusion image after registration of the left ventricle of the heart (left lateral).

Referring to FIG. 11, 1105 is illustrative of lesion locations demonstrated on a Fast Anatomical Mapping-derived image and 110 is illustrative of lesion locations demonstrated on a Fast Anatomical Mapping-derived image. Lesion locations demonstrated on SPECT-MDCT fusion images are shown in 1115 and 1120 is illustrative of lesion locations demonstrated on SPECT-MDCT fusion images.

Images were acquired using a commercial dual-headed gamma scintillation camera (Philips Medical Systems Inc., Milpitas, Calif., USA) after administration of high-dose (30 mCi) Tc-99m Sestamibi using standard myocardial perfusion imaging parameters (20% acceptance window around 140 keV energy peak, 180° orbit, 32 steps with 25 sec of data acquisition per step), and reconstructed iteratively using maximum likelihood expectation maximization algorithm with a post-processing Butterworth filter. Images were processed using a commercial software package (Segment, version 1.9 R1917, Medviso, Lund, Sweden). The myocardium-at-risk tools described by Soneson et al. were adapted, in which perfusion defect extent is based on an a priori model of coronary artery distribution and using a cutoff of <55% of maximal counts from the individual patient. Percent area under threshold, which combines defect extent and severity, was used to define regions of scar. Scar information was spatially mapped onto a three dimensional reconstruction of the endocardial left ventricle contour derived from summed resting stack. In slices where the right ventricle was visible on SPECT, manual contours were drawn and exported to serve as an anatomical reference.

End-expiratory images were obtained using a commercial 64-row scanner (GE-VCT, GE Medical Systems, Milwaukee, Wis.) with adaptive iterative reconstruction (ACIR) software. After initial localizing images, CT angiography of the heart was obtained with 150 cc intravenous Iodixanol (GE Medical Systems, Milwaukee, Wis.) timed for the aortic root utilizing test bolus technique using the following parameters: prospective ECG-triggered acquisition centered on 75% RR with 50 msec padding, 0.63 mm slice collimation, 120 kvp, 40 mA with 40% ACIR. All images were transferred to a GE AW workstation with 4.6 platform software for off-line post-processing. Volume rendered views of the left ventricle, right ventricle, and left atrium were separately segmented and exported.

The reconstructed SPECT left ventricle image was "warped" so as to geometrically match that derived from MDCT using a proprietary iterative affine transformation algorithm (QuantMD Inc., Pittsburgh, Pa., USA). The SPECT- and CT-derived images relating to the right ventricle were used to establish rotational correspondence. SPECT data was then transferred to the MDCT image (as in FIG. 6).

Monomorphic VT was easily inducible and was poorly tolerated hemodynamically. All subsequent mapping and ablation was performed during sinus rhythm, with the assistance of a commercial catheter navigation system (Carto® 3, Biosense, Diamond Bar, Calif.). Using a multielectrode catheter (Thermocool®, Biosense Webster) and Fast Anatomical Mapping software, partial endocardial casts of the left ventricle, right ventricle, left atrium, and aortic root were created in approximately 15 minutes (total) and were used to register the SPECT-MDCT left ventricle fusion image without the use of body surface fiducials (FIG. 10). Subsequently, the left venticle endocardium was extensively sampled to create a left ventricle electroanatomic image in which scar and scar border tissues were defined by filtered (40-500 Hz) bipolar peak amplitudes of <0.5 millivolts and 0.5-1.5 millivolts, respectively. This process took approximately 45 minutes. There was marked spatial correspondence between the fusion and electroanatomic images of the left ventricle (FIG. 10). Focal ablation lesions were applied contiguously to encompass the entire border tissue mass, after which VT was no longer inducible (FIG. 11). At 6 months after the procedure and free of all antiarrhythmic agents, this patient has experienced no further VT.

This example illustrates the feasibility of using a SPECT-MDCT "fusion" image for guiding left ventricle substrate ablation. This novel technique may provide a number of advantages. First, MDCT provides a detailed, personalized representation of the left ventricle endocardial (including chordal-papillary apparatus) and epicardial (including coronary vasculature and fat) anatomies, which are not well represented by electroanatomic techniques, even with extensive effort. Second, combining MDCT and SPECT data is synergistic, given that MDCT does not locate left ventricle scar well, whereas SPECT does but does not output data in an anatomically accurate fashion. Third, as is demonstrated here, the spatial specificity provided by cursory fast anatomical mapping of the left ventricle and contiguous structures appears adequate for accurate image registration without body surface fiducials. Detailed substrate information is thus available quickly, as opposed to the time consuming and often technically challenging and fatiguing method of characterization using direct sampling. In addition, direct sampling may only provide an indirect and thus potentially muted assay of the substrate assay, as with electrogram amplitude. Finally, the fusion technique is adaptable, permitting it to include other imaging modalities, including echocardiography, MRI, and PET. Two or more techniques may be fused, emphasizing the strengths of each. Developments in the content of individual imaging modalities may permit improved targeting based on anatomic/functional details, or on more fundamental (cellular or biochemical) processes underlying an anatomic substrate.

Example 2

Many patients referred for CRT fail to improve following device deployment, in part due to poor left ventricular lead placement. FIGS. 12-16 illustrate the capabilities of a method of the present disclosure for applying a fused image to the guidance of left ventricle lead placement during device implantation.

Five consecutive patients with ischemic cardiomyopathy and left bundle branch block (N=2), a previously implanted dual-chamber pacemaker (N=1), or atrial fibrillation undergoing atrioventricular nodal ablation (N=2), were referred for clinically indicated SPECT and CT imaging studies prior to CRT implantation/upgrade. Clinical characteristics were obtained from review of the electronic records. A preoperative 12-lead electrocardiogram was obtained and QRS duration was measured as the longest among 12 leads; the average duration over 10 non-consecutive beats was utilized. Our study protocol was approved by the Institutional Review Board of the University of Pittsburgh Medical Center.

Resting SPECT images were acquired using a commercial dual-headed gamma scintillation camera (Philips Medical Systems Inc., Milpitas, Calif., USA) after administration of high-dose (30 mCi) Tc-99m Sestamibi using standard myocardial perfusion imaging parameters (20% acceptance window around 140 keV energy peak, 180° orbit, 32 steps with 25 sec of data acquisition per step). Gated tomograms were acquired with 16 frames (64 projections per frame) per RR interval, and reconstructed iteratively using maximum likelihood expectation maximization algorithm with a post-processing Butterworth filter.

Figure 12:
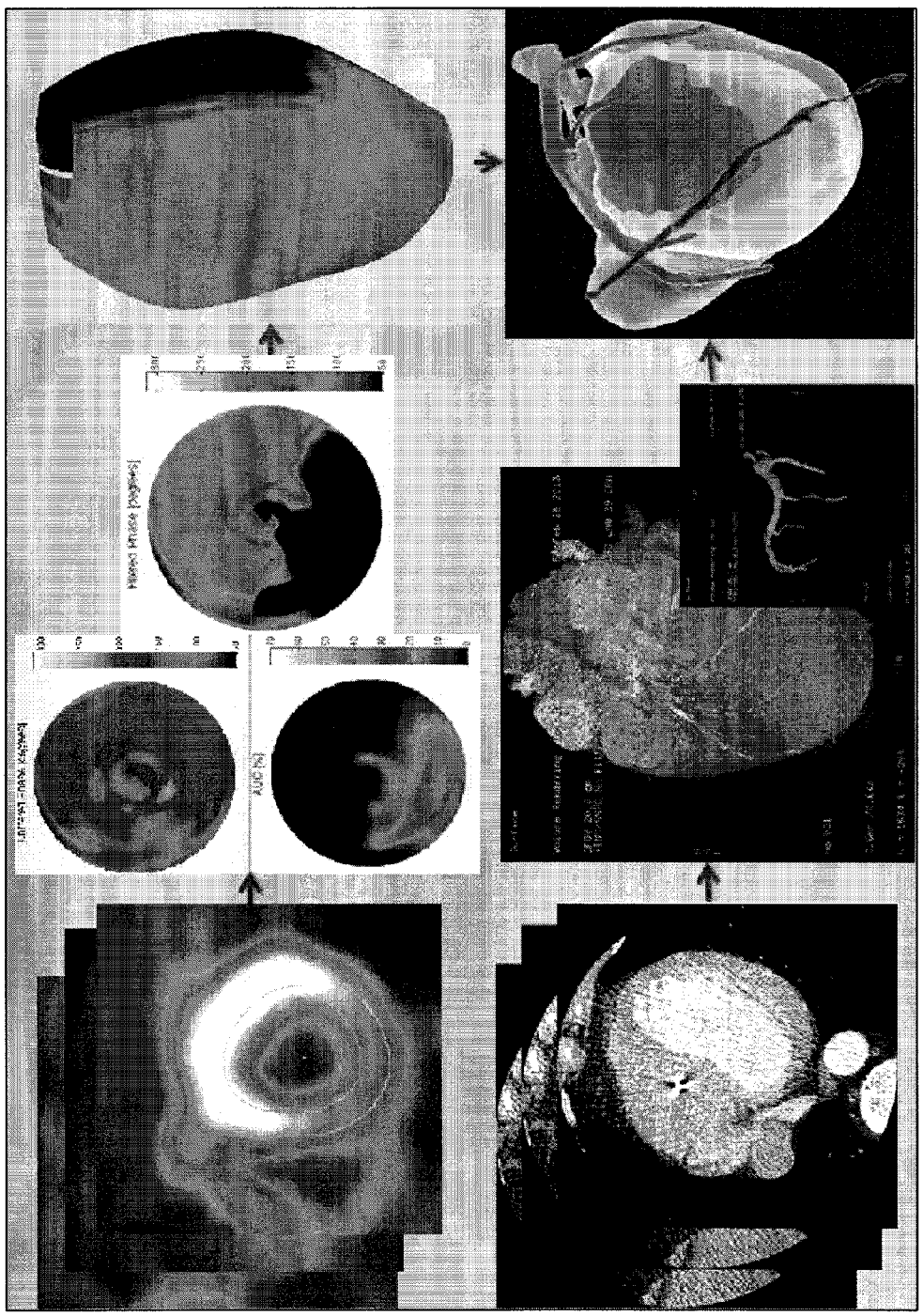
FIG. 12 is representative of the fusion capabilities of the present disclosure.

SPECT images were processed using a commercial software package (Segment, version 1.9 R1917, Medviso, Lund, Sweden; http://segment.heiberg.se). To identify scar, the myocardium-at-risk tools described by Soneson et al were adapted, in which perfusion defect extent is based on an a priori model of coronary artery distribution and using a cutoff of <55% of maximal counts from the individual patient. Percent area under threshold, which combines defect extent and severity, was used to define regions of scar. Activation information was derived from phase analysis of gated, shot-axis images. Automated segmentation of gated images was performed as previously described using known methods. The left ventricle myocardium was divided into 8 segments per short-axis slice, yielding >120 sectors in total, and a normalized time-activity profile (16 frames per cycle) was derived for each sector. Fast Fourier transform performed on all sectors yielded maximal thickening (contraction) by the phase of the first harmonic. Phase and scar information were coalesced by blacking out regions with scar and displayed in polar map format (FIG. 12).

MDCT was performed using a 64-row MDCT scanner, GE-VCT (GE Medical Systems, Milwaukee, Wis.). An adaptive iterative reconstruction (ACIR) software was employed. Localizing images were obtained, followed by CT venography of the heart using 150 cc intravenous Iodixanol (GE Medical Systems) timed for the coronary veins using a test bolus technique. Imaging parameters were as follows: prospective ECG-triggered acquisition centered on 75% of RR with 50 milliseconds padding, 0.63 mm slice collimation, 120 kvp, 40 mA with 40% ACIR. Images were transferred to a GE AW workstation (Platform 4.6; GE Medical Systems) for off-line post-processing. The whole heart, left ventricle wall, right ventricular cavity, and coronary veins were separately segmented and exported. The phrenic nerve was also identified where visible and segmented.

Phase and scar information computed from SPECT images were spatially mapped onto a three dimensional reconstruction of the left ventricle epicardial contour derived from the summed SPECT data. In slices where the right ventricle was visible on SPECT, manual contours were drawn and exported to serve as an anatomical reference. The colored SPECT-derived left ventricle shell was "warped" to match the epicardial surface of the CT-derived left ventricle using an in-house, automated, affine transformation algorithm establishing surface correspondences between the two surfaces (still referring to FIG. 12). The SPECT right ventricle shell was used for estimation of rotational correspondence about the left ventricle axis, as a means of crudely registering the two surfaces prior to establishing surfaces correspondence. Following this step, the SPECT-derived color information was transferred onto the CT-derived left ventricle. The transferred colors delineated both scar and activation timing of the left ventricle, as described above. Both scar and a target site were demarcated as outlines on the left ventricle model, in order to distinguish between these territories as different colored regions in the NavX environment (still referring to FIG. 12).

Figure 13:
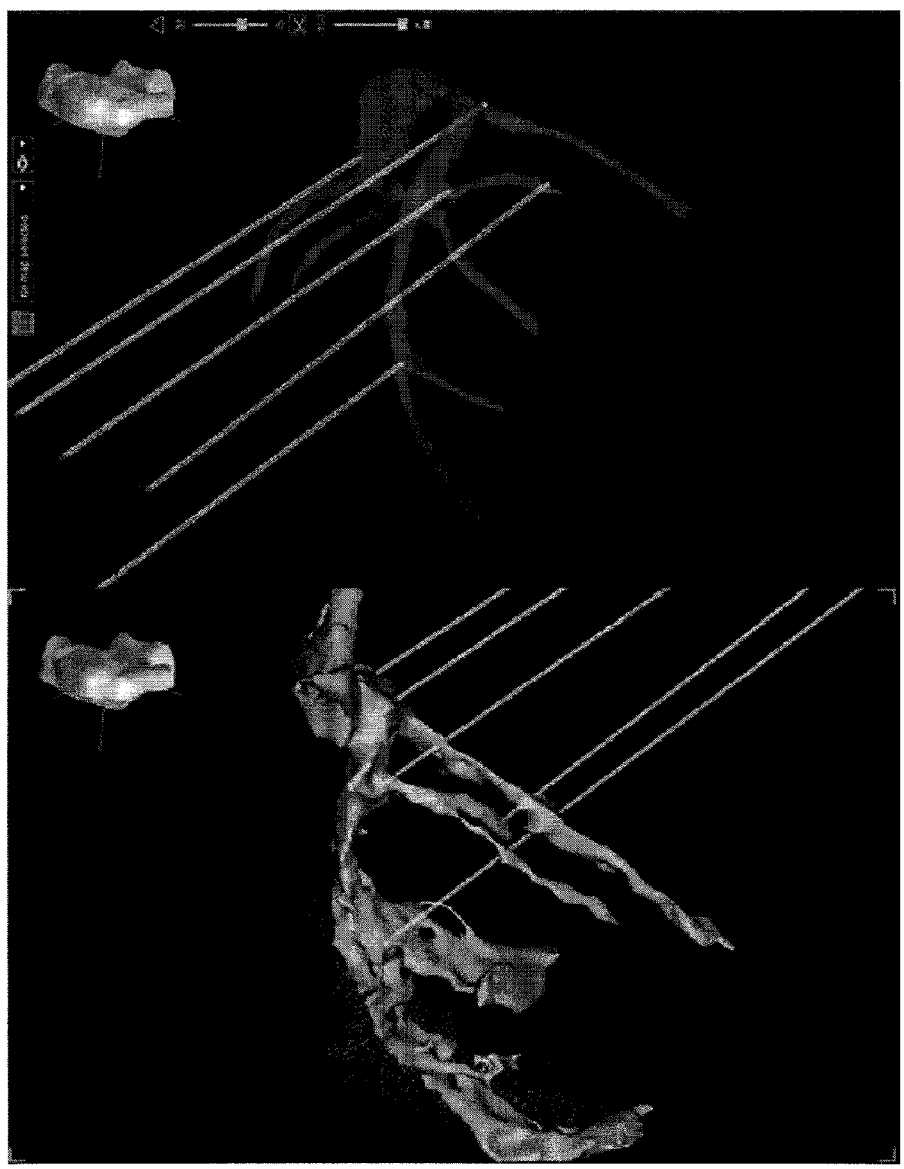
FIG. 13 is representative of a virtual venogram and operative registration.

The Ensite NavX Velocity (St. Jude Medical) system was used for operative left ventricle lead guidance. This system utilizes three cutaneous patches to create 5.7 kHz electrical fields in the thoracic space that are sensed by any cardiac electrode, such as those on an electrophysiology catheter or pacing lead. The electrode position is calculated and portrayed in real time based on the sensed potentials emanating from the cutaneous patches. Access was gained to the existing left pre-pectoral pocket if present. Separate access to the central circulation was gained via extra-thoracic venipuncture. An introducer sheath was placed into the proximal coronary sinus, and used to deliver a bipolar catheter (Biotronik), which was connected to NavX and used to explore the coronary venous anatomy and right ventricle. The location of the catheter was tracked and recorded continuously at end-expiration and used to create a 'virtual venogram'. Continuous point acquisition gated to the QRS complex enabled the acquisition of voltage and electrical activation times, which were analyzed post-operatively. No contrast venography was performed. The SPECT-CT model was registered to the operative space using manual point-by-point (<25 in total) correspondence of the coronary venous anatomy on the virtual venogram and the coronary veins from CT. The result is illustrated by FIG. 13.

The introducer sheath was used to deliver standard left ventricle leads which were navigated in real time into a branch of the coronary venous system to the pre-specified target site that was late-activating and free of scar. The lead was connected to a CRT pulse generator that was implanted into the pocket. Intra-operative right anterior oblique (RAO, 30°) and left anterior oblique (LAO, 60°) fluoroscopic images were obtained to confirm final lead location. Phrenic nerve and activation thresholds were assessed for each pacing electrode.

Figure 14:
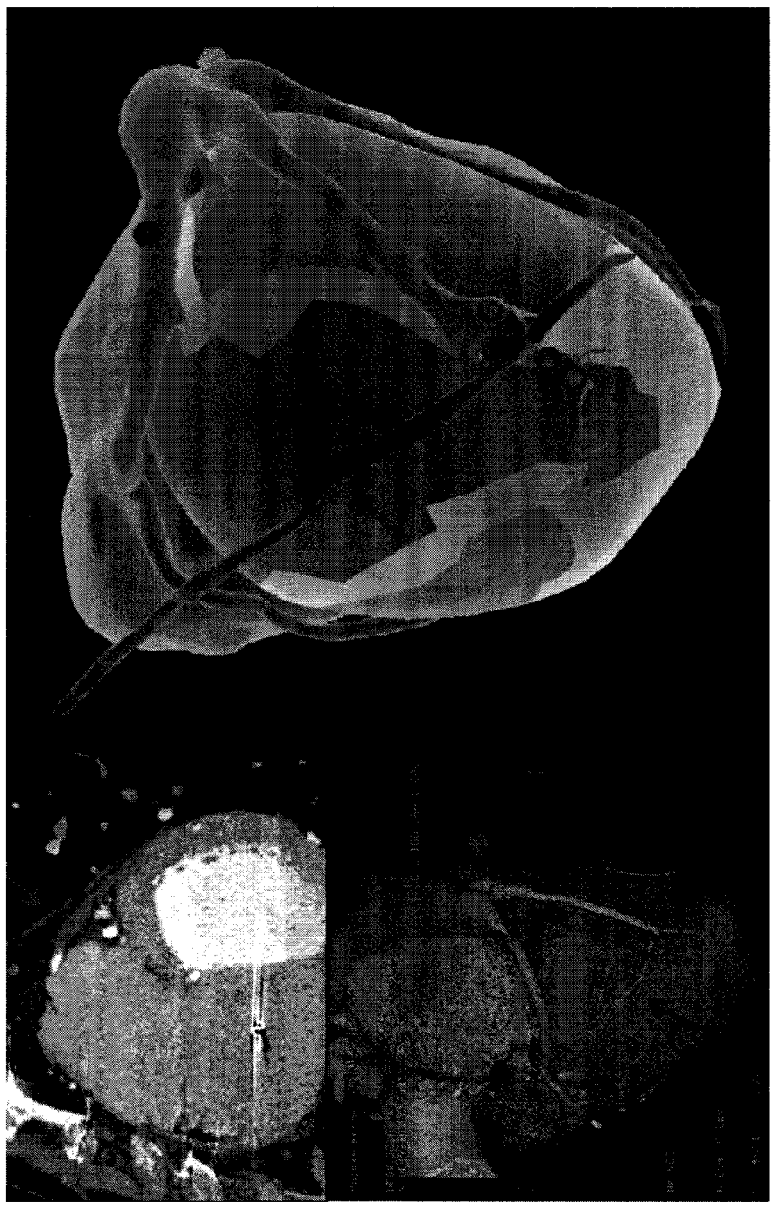
FIG. 14 is representative of the fusion capabilities of the present disclosure.
Figure 15:
FIG. 15 is representative of the fusion capabilities of the present disclosure.
Figures 16A, 16B:
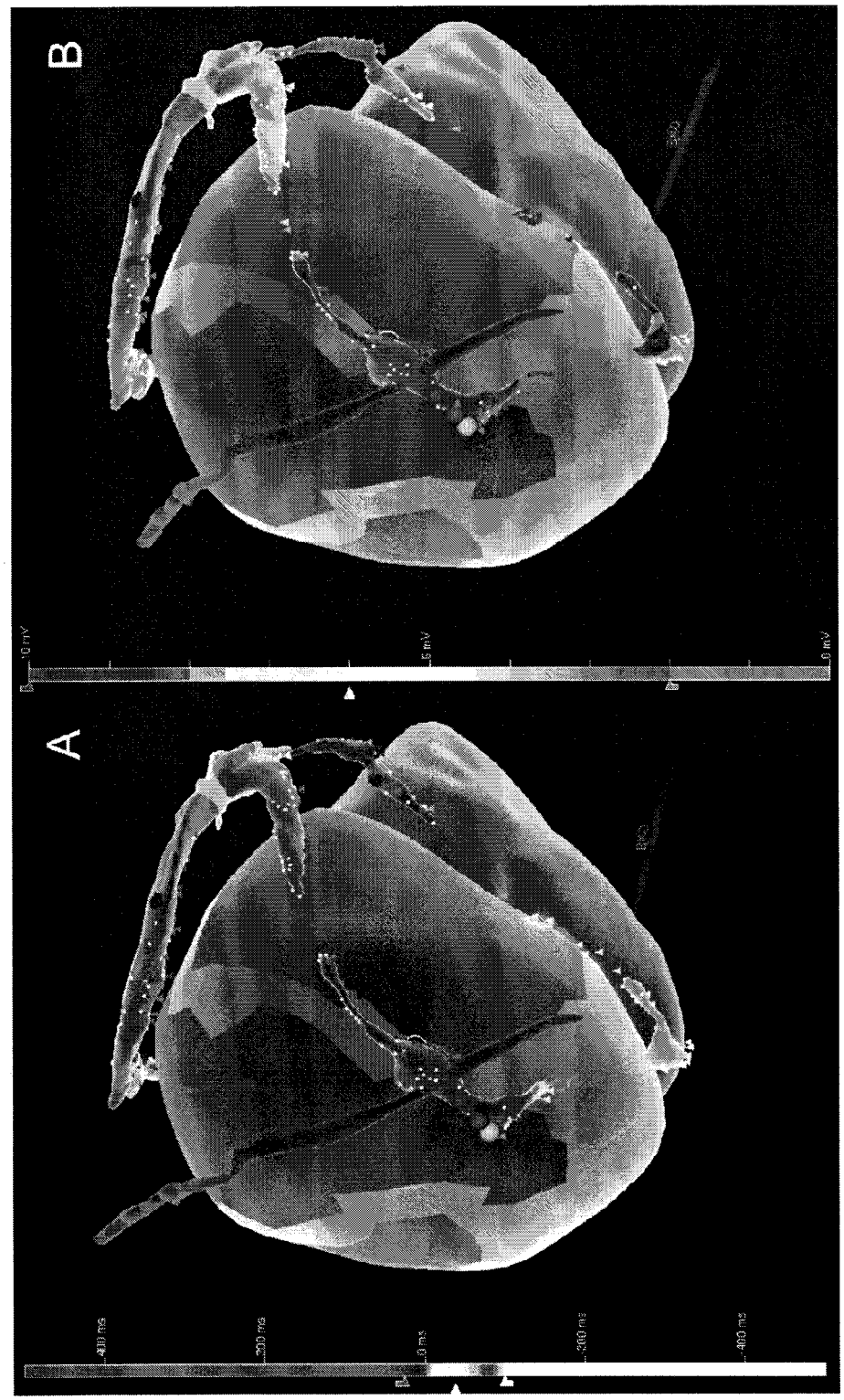
FIG. 16A and FIG. 16B is representative of the fusion capabilities of the present disclosure.

Pre-operative and operative protocol were completed for each of five cases. The total mapping time for virtual venography averaged about 15 minutes, requiring roughly 5 additional minutes of fluoroscopy. No other adjustment to the standard workflow was necessary. A complete venous tree was extracted for 4 of 5 patients, with the fifth limited by image quality. Significant dyssynchrony assessed by pre-operative SPECT was present in both patients with LBBB and the patient who was right ventricle paced, but neither patient with a narrow QRS. The phrenic nerve was identified and segmented in 4 of 5 patients, as illustrated by FIG. 14. In cases where the phrenic nerve crossed the target vessel, the course of the phrenic nerve was verified by diaphragmatic stimulation thresholds. Intra-operative RAO and LAO fluoroscopic images were obtained to confirm that the location of the left ventricle lead was in the target location. This is illustrated in FIG. 15. In cases where the pre-operative SPECT showed dyssynchrony or scar, our pre-operative model was visually compared to activation and voltage maps obtained from the roving bipolar catheter, and a strong correspondence was observed. This is illustrated by FIGS. 16A (correspondence of site of latest activation from SPECT and electrical maping) and FIG. 16B (scar from SPECT with voltage).

Example 2 demonstrates the feasibility of intra-operative left ventricle lead guidance using pre-operatively acquired SPECT and CT images. In five patients, the left ventricle lead was successfully directed to a late-activating region that was free of scar, without compromise to the standard CRT workflow. The feasibility of using this technique to address relevant clinical questions regarding the correspondence between mechanical and electrical activation information and scar and voltage information is also demonstrated. Furthermore, this technique may serve as a useful platform for assessing the impact of pacing site and lead proximity to scar on left ventricle hemodynamics.

Pre-operative cardiac CT was used for its excellent visualization of the coronary venous anatomy and anatomic fidelity and SPECT for its ability to readily supply activation and scar information in three dimensions. While CT does come at the cost of additional radiation, it provides valuable information that can be used for surgical planning. For instance, a patient that has no suitable vein in a region free of scar could be referred for a transthoracic, rather than transvenous, implantation. CT also allowed for visualization of the phrenic nerve the majority of cases, which was displayed to the surgeon during the procedure to aid in lead guidance. Furthermore, many patients are not candidates for cardiovascular magnetic resonance (CMR) imaging, including patients with an existing implantable pacing device or renal failure, which may represent as many as 50% of patients referred for CRT. Pre-operative CT is already the standard of care for many cardiac electrophysiology procedures.

While the disclosure has been described in detail in reference to specific embodiments thereof, it will be apparent to one skilled in the art that various changes and modifications can be made therein without departing from the spirit and scope of the embodiments. Additionally, while the examples provided herein related to cardiac interventions, the present disclosure is not limited to these interventions and may be applied in a wide variety of surgical and clinical procedures. Thus, it is intended that the present disclosure cover the modifications and variations of this disclosure provided they come within the scope of the appended claims and their equivalents.

What is claimed is:

1. A method for aiding cardiac and other surgical interventions comprising:
    acquiring at least one medical imaging data set representative of at least one biological sample,
    wherein the biological sample comprises at least one structure, and
    wherein each medical imaging data set comprises volume image data comprising a plurality of voxels representative of data in at least three dimensions and wherein each volume image comprises a plurality of two-dimensional image planes comprising a plurality of pixels;
    segmenting a first set of volume image data comprising a plurality of voxels associated with at least one structure of the biological sample to generate a surface comprising a plurality of points;
    selecting a second set of volume image data comprising a plurality of voxels associated with at least one characteristic of the biological sample, wherein the characteristic is a magnitude of at least one physically relevant parameter of the sample, wherein the magnitude is expressed as at least one color;
    selecting a plurality of spatial fiducial markers on the surface and a plurality of spatial fiducial markers on the second set of volume image data;
    applying at least one rigid transformation to spatially transform the second set of volume image data into a virtual spatial location comprising the segmented structure using the plurality of spatial fiducial markers;
    applying at least one non-rigid transformation to warp at least a portion of the second set of volume image data onto the surface;
    applying at least one nearest neighbor algorithm to correlate each of a plurality of points of the surface with at least one voxel associated with the second set of volume image data; and
    re-sampling the second set of volume image data onto the surface at each of a plurality of points based on this correlation to generate a fused image, wherein the fused image comprises a color image representative of the surface, wherein each color is indicative of at least one characteristic at that location in the biological sample.

2. The method of claim 1 further comprising analyzing the fused image to generate a surgical intervention plan.

3. The method of claim 1 further comprising analyzing the fused image to guide at least one surgical intervention.

4. The method of claim 3 wherein the surgical intervention further comprises at least one cardiac surgical intervention.

5. The method of claim 3 wherein the surgical intervention further comprises at least one non-cardiac surgical intervention.

6. The method of claim 3 further comprising co-registering the fused image with at least one location of a patient's body intra-operatively.

7. The method of claim 6 wherein the co-registration is achieved by associating the fused image with at least one surgical tool, wherein the surgical tool is electromagnetically tracked within the patient's body.

8. The method of claim 1 wherein the magnitude further comprises a range of values and wherein the color further comprises an arbitrary color gradient correlated with the range of values.

9. The method of claim 1 wherein the non-rigid transformation further comprises a thin-plate splines method.

10. The method of claim 1 wherein at least one medical imaging data set is further generated pre-operatively.

11. The method of claim 1 wherein at least one medical imaging data set is further generated intra-operatively.

12. The method of claim 1 wherein the fused image is generated pre-operatively.

13. The method of claim 1 wherein the fused image is generated intra-operatively.

14. The method of claim 1 wherein at least two medical imaging data sets are acquired using one medical imaging modality.

15. The method of claim 1 wherein at least two medical imaging data sets are acquired using at least two different imaging modalities.

16. The method of claim 1 wherein the medical imaging data set is further acquired using at least one of the following imaging modalities: CMR, SPECT, CT, MRI, PET, x-ray, and fluoroscopy.

17. A method for aiding cardiac and other surgical interventions comprising:
  acquiring at least one medical imaging data set representative of at least one biological sample,
    wherein the biological sample comprises at least one structure, and
    wherein each medical imaging data set comprises volume image data comprising a plurality of voxels representative of data in at least three dimensions and wherein each volume image comprises a plurality of two-dimensional image planes comprising a plurality of pixels;
  segmenting a first set of volume image data comprising a plurality of voxels associated with at least one structure of the biological sample to generate a surface comprising a plurality of points;
  selecting a second set of volume image data comprising a plurality of voxels associated with at least one characteristic of the biological sample, wherein the characteristic is a magnitude of at least one physically relevant parameter of the sample, wherein the magnitude is expressed as at least one color;
  selecting a plurality of spatial fiducial markers on the surface and a plurality of spatial fiducial markers on the second set of volume image data;
  converting the second set of volume image data into a standard form, wherein each point on the standard form maintains the characteristic data;
  applying at least one rigid transformation to spatially transform the standard form into a virtual spatial location comprising the structure using the plurality of spatial fiducial markers;
  applying at least one non-rigid transformation to warp at least a portion of the standard form onto the surface using the plurality of fiducial markers;
  applying at least one nearest neighbor algorithm to correlate each of a plurality of points of the surface with at least one point on the standard form; and
  re-sampling the second set of volume image data onto the surface at each of a plurality of points based on this correlation to generate a fused image, wherein the fused image comprises a color image representative of the surface, wherein each color is indicative of at least one characteristic at that location in the biological sample.

18. The method of claim 17 further comprising analyzing the fused image to generate a surgical intervention plan.

19. The method of claim 17 further comprising analyzing the fused image to guide at least one surgical intervention.

20. The method of claim 19 wherein the surgical intervention further comprises at least one cardiac surgical intervention.

21. The method of claim 19 wherein the surgical intervention further comprises at least one non-cardiac surgical intervention.

22. The method of claim 19 further comprising co-registering the fused image with at least one location of a patient's body intra-operatively.

23. The method of claim 22 wherein the co-registration is achieved by associating the fused image with at least one surgical tool, wherein the surgical tool is electromagnetically tracked within the patient's body.

24. The method of claim 17 wherein the magnitude further comprises a range of values and wherein the color further comprises an arbitrary color gradient correlated with the range of values.

25. The method of claim 17 wherein the non-rigid transformation further comprises a thin-plate splines method.

26. The method of claim 17 wherein at least one medical imaging data set is further generated pre-operatively.

27. The method of claim 17 wherein at least one medical imaging data set is further generated intra-operatively.

28. The method of claim 17 wherein the fused image is generated pre-operatively.

29. The method of claim 17 wherein the fused image is generated intra-operatively.

30. The method of claim 17 wherein at least two medical imaging data sets are acquired using one medical imaging modality.

31. The method of claim 17 wherein at least two medical imaging data sets are acquired using at least two different imaging modalities.

32. The method of claim 17 wherein the medical imaging data set is further acquired using at least one of the following imaging modalities: CMR, SPECT, CT, MRI, PET, x-ray, and fluoroscopy.

33. A method for aiding cardiac and other surgical interventions comprising:
  acquiring at least one medical imaging data set representative of at least one biological sample,
    wherein the biological sample comprises at least one structure, and
    wherein each medical imaging data set comprises volume image data comprising a plurality of voxels representative of data in at least three dimensions and wherein each volume image comprises a plurality of two-dimensional image planes comprising a plurality of pixels;
  segmenting a first set of volume image data comprising a plurality of voxels associated with at least one structure of the biological sample to generate a surface comprising a plurality of points;
  selecting a second set of volume image data comprising a plurality of voxels associated with at least one characteristic of the biological sample, wherein the characteristic is a magnitude of at least one physically relevant parameter of the sample, wherein the magnitude is expressed as at least one color;
  selecting a plurality of spatial fiducial markers on the surface and a plurality of spatial fiducial markers on the second set of volume image data;
  converting the second set of volume image data into a standard form, wherein each point on the standard form maintains the characteristic data;
  transforming the standard form into a third set of volume image data comprising a plurality of voxels representative of data in at least three dimensions and wherein each voxel is associated with at least one characteristic;
  transforming the surface onto the third set of volume image data using the plurality of spatial fiducal markers;
  applying a nearest neighbor algorithm to correlate each of a plurality of points of the surface with at least one voxel of the third set of volume image data; and re-sampling the third set of volume image data onto the surface at each of a plurality of points based on this correlation to generate a fused image, wherein the fused image comprises a color image representative of the surface, wherein each color is indicative of at least one characteristic at that location in the biological sample.

34. The method of claim 33 further comprising analyzing the fused image to generate a surgical intervention plan.

35. The method of claim 33 further comprising analyzing the fused image to guide at least one surgical intervention.

36. The method of claim 35 wherein the surgical intervention further comprises at least one cardiac surgical intervention.

37. The method of claim 35 wherein the surgical intervention further comprises at least one non-cardiac surgical intervention.

38. The method of claim 35 further comprising co-registering the fused image with at least one location of a patient's body intra-operatively.

39. The method of claim 38 wherein the co-registration is achieved by associating the fused image with at least one surgical tool, wherein the surgical tool is electromagnetically tracked within the patient's body.

40. The method of claim 33 wherein the magnitude further comprises a range of values and wherein the color further comprises an arbitrary color gradient correlated with the range of values.

41. The method of claim 33 wherein the non-rigid transformation further comprises a thin-plate splines method.

42. The method of claim 33 wherein at least one medical imaging data set is further generated pre-operatively.

43. The method of claim 33 wherein at least one medical imaging data set is further generated intra-operatively.

44. The method of claim 33 wherein the fused image is generated pre-operatively.

45. The method of claim 33 wherein the fused image is generated intra-operatively.

46. The method of claim 33 wherein at least two medical imaging data sets are acquired using one medical imaging modality.

47. The method of claim 33 wherein at least two medical imaging data sets are acquired using at least two different imaging modalities.

48. The method of claim 33 wherein the medical imaging data set is further acquired using at least one of the following imaging modalities: CMR, SPECT, CT, MRI, PET, x-ray, and fluoroscopy.

* * * * *